the present invention provides a method, which can be operated continuously and has a wide scope of application, for destructing part of fines in slurry in a crystallizer to obtain large crystals having high purity and large crystal size, characterized in that first and second filters are installed in the crystallizer, a part of slurry containing only fines of size smaller than the fines cut size is drawn from the crystallizer, through the first filter in the crystallizer to a fines destruction loop for destructing the fines and then to the crystallizer through the second filter in the crystallizer by using a circulating pump. The two filters are switched over at regular interval and washed with each other's effluent to ensure the cintinuous operation of the above process.

United States Patent [19]

Zhang et al.

[11] Patent Number: 5,663,456
[45] Date of Patent: Sep. 2, 1997

[54] METHOD FOR OBTAINING LARGE CRYSTALS WITH HIGH PURITY BY DESTRUCTING PART OF FINES IN SLURRY IN A CRYSTALLIZER

[75] Inventors: Minhua Zhang; Zongzhang Liu; Shenbo Yu; Chuanzhao Li; Shenghua Qian, all of Tianjin, China

[73] Assignees: China Petro-Chemical Corporation, Beijing; Tianjin University, Tianjin, both of China

[21] Appl. No.: 501,137
[22] PCT Filed: Feb. 16, 1994
[86] PCT No.: PCT/CN94/00013
   § 371 Date: Dec. 26, 1995
   § 102(e) Date: Dec. 26, 1995
[87] PCT Pub. No.: WO94/19083
   PCT Pub. Date: Sep. 1, 1994

[30] Foreign Application Priority Data

Feb. 17, 1993 [CN] China ................ 93101419.0

[51] Int. Cl.⁶ .............................. C07C 37/84
[52] U.S. Cl. ........................................... 568/724
[58] Field of Search ........................ 568/728, 724

[56] References Cited

U.S. PATENT DOCUMENTS

| | | | |
|---|---|---|---|
| 3,900,292 | 8/1975 | Fairchild | 23/273 R |
| 3,992,900 | 11/1976 | Campbell | 62/541 |
| 3,996,018 | 12/1976 | Midler, Jr. | 23/295 R |
| 4,159,194 | 6/1979 | Steward | 23/301 |
| 4,263,010 | 4/1981 | Randolph | 23/230 A |
| 4,670,611 | 6/1987 | Lemay | 568/868 |
| 4,735,781 | 4/1988 | Thijssen et al. | 422/251 |
| 5,043,071 | 8/1991 | Anselme et al. | 210/636 |
| 5,074,999 | 12/1991 | Drori | 210/143 |
| 5,124,265 | 6/1992 | Randolph | 436/55 |
| 5,147,412 | 9/1992 | Klinksiek et al. | 23/293 R |

Primary Examiner—José G. Dees
Assistant Examiner—Barbara Badio
Attorney, Agent, or Firm—Chilton, Alix & Van Kirk

[57] ABSTRACT

The present invention provides a method, which can be operated continuously and has a wide scope of application, for destructing part of fines in slurry in a crystallizer to obtain large crystals having high purity and large crystal size, characterized in that first and second filters are installed in the crystallizer, a part of slurry containing only fines of size smaller than the fines cut size is drawn from the crystallizer, through the first filter in the crystallizer to a fines destruction loop for destructing the fines and then to the crystallizer through the second filter in the crystallizer by using a circulating pump. The two filters are switched over at regular interval and washed with each other's effluent to ensure the cintinuous operation of the above process.

The present invention also provides a method for preparing crystalline bisphenol A/phenol adduct and bisphenol A with high purity and large crystal size.

15 Claims, 1 Drawing Sheet

METHOD FOR OBTAINING LARGE CRYSTALS WITH HIGH PURITY BY DESTRUCTING PART OF FINES IN SLURRY IN A CRYSTALLIZER

FIELD OF THE INVENTION

The present invention relates to a method for obtaining large crystals with high purity by destructing part of the fines formed during crystallization, the application of said method, more particularly, a method for obtaining a crystalline product with large and uniform crystal size and high purity by effectively destructing a part of lines in slurry in a crystallizer by using special filters in the crystallizer and a special fines destruction loop outside the crystallizer and the application of the said method in the preparation of bisphenol A with high purity.

BACKGROUND OF THE INVENTION

According to the theory of solution crystallization, the purity of a crystalline product relies on the crystal size distribution to a large extent. Particularly, the purity of a crystalline product is greatly influenced by the fraction of fines. An increase in the fines fraction inevitably results in an increase in the crystal surface area per unit weight. This not only increases the amount of impure mother liquor entrained by the crystals, but also diminishes the benefit of filtering and washing operations. Consequently, it is difficult to obtain a high purity product in one stage crystallization and generally multi-stage crystallization is needed, causing unnecessary waste. Many studies support this finding. Therefore, in order to improve the product purity or obtain the greatest possible benifit from washing and filtering operations, it would be desirable to obtain a crystalline product with a large and uniform crystal size in the crystallization process.

In a continuous or batch crystallizer, crystal particles are formed as a result of the growth of individual crystal nuclei. In a fixed amount of slurry, if the number of the crystal nuclei is too large, the crystal size of the final product must be small since a limited mount of solute is distributed over excessive crystal nuclei. Therefore, it is necessary to destruct the excessive crystal nuclei in time. An effective destruction of fines is beneficial not only for increasing the mean crystal size of the product, but also for raising the crystal growth rate, because in a crystallizer with a fines destruction system the degree of supersaturation may be somewhat increased, and hence both the crystal growth rate and the production capacity of the crystallizer are improved.

The existing methods for destructing fines are the setting method based on elutriation theory and the size fractionation method, for example, see the following reference:

Randolph, A. D., Larson, M. A. Theory of Particulate Processes, Academic Press, New York, 1988; Nyrlt, J., Industrial crystallization. The state of Art; VCH, Weinheim, 1982; U.S. Pat. Nos. 3,873,275; 5,124,265; Qing Xu-huai and Tan Qiu, Industrial Crystallization, Chemical Industry Press, Beijing, 1985. The settling method requires an annular baffle set in the crystallizer to form a settling zone. However, the presence of the settling zone not only increases the complicacy of the crystallizer structure, but also reduces the effective volume and the production capacity of the crystallizer. Moreover, it is difficult to apply the settling method to a crystallization processes which is carried out under vacuum, pressure or by evaporation. In brief, the settling method is troublesome in operation and poor in adaptability. On the other hand, the size fractination method requires complicated equipments and demonstrates poor suitability. In addition, both the above methods are essentially unsuitable to those systems in which the density difference between solid and liquid is small.

SUMMARY OF THE INVENTION

The object of the present invention is to provide a method for overcoming the disadvantages of the prior art mentioned above and for obtaining large crystals with high purity by destructing part of the fines in a slurry.

Another object of the present invention is to obtain a bisphenol A product with high purity by using the present method in the preparation of bisphenol A.

As a result of an extensive study carried out by the inventors, it was found that the said objects can be achieved by using special filters in a crystallizer which includes a special fines destruction loop.

The present invention provides a method, which is easily implemented and has a wide scope of application, for continuously destructing the fines in slurry in a crystallizer to obtain a crystalline product with high purity and large crystal size. The said method comprises the following steps:

A. two filters are installed in the crystallizer;
B. a part of the slurry in the crystallizer is filtered through the first filter using circulating pump, and a slurry containing fines, substantially all of which are of a size smaller than the fines cut size, is fed to at least one fines destructor in which they are dissolved, and then the solution in which the fines have been destructed is fed back to the crystallizer through the second filter for further crystallization;
C. after a switching interval, a part of the slurry in the crystallizer is filtered through the second filter using a circulating pump, a slurry containing fines, substantially all of which are of a size smaller than the fines cut size, is fed to at least one fines destructor in which they are dissolved, and then the solution in which the fines have been destructed is fed back to the crystallizer through the first filter for further crystallization, thereby washing the first filter; and
D. after a switching interval, repeating procedure B and thereby washing the second filter, and continuing to alternately repeat the procedures B and C to carry out the process of destructing fines continuously.

The crystallizers used in the present invention include various types and configurations of crystallizers. The preferred crystallizers finclude a cooling crystallizer, such as a stirring crystallizer, a Swenson-walker crystallizer and a Cerny direct-coolant crystallizer; an evaporating crystallizer; a salting crystallizer; a reaction crystallizer and a vacuum crystallizer etc.

The filters used in the present invention comprise various types and configurations of hollow cavities being able to allow fines of size smaller than the cut size to pass through, for example, porous hollow cylinder, spheroid-and table-types of sterofilter covered with or without filter cloth. The most preferred filter is a filter consisting of a porous hollow cylinder and knitmesh materials covered with the cylmder materials. The said hollow cylinder can be made of metal, ceramics or polymer, depending on the treated materials. The knitmesh materials can be made of metal wire or glass fiber, or a kind of fabrics made from synthetic fiber or natural fiber such as cotton, wood, silk, hemp.

The said knitmesh has a definite pore size to allow the crystals of size smaller than the cut size to pass through, which is decided by the fines cut size, i.e. the maximum size of the fines expected to be destructed. The fines cut size can be controlled by using knitmesh material with different pore size to cover the porous hollow cylinder.

The filters can be installed at any location below the liquid level of the slurry. Preferably the two filters are immersed vertically and oppositely in the upper part of the slurry.

The fines destructors used in the present invention are various heat-exchangers being able to dissolve the fines by heating or solvent, preferably shell and tube exchanger, coil heat exchanger or jacketed heat exchanger. In addition, when the fines are dissolved by the solvent, the present invention may use exchanger with or without heating.

In the present method, either one or two fines destructors may be used, depending on the performance of the circulating pump itself and the influence of the crystals on the circulating pump. When two fines destructors are used, they may or may not be the same, and the circulating pump is installed between the two fines destructors; when one fines destructor is used, the circulating pump may be installed either before or behind the destructor.

The present method is applicable to crystallization processes of various solute-solvent systems the said solutes comprise those which can not be obtained in high purity and/or large crystal size by coventional crystallization process, such as bisphenol A/phenol adduct and bisphenol A. The said solvents include water; alcohols, such as methanol, ethanol; esters, such as ethyl acetate; ethers, such as diethyl ether, tetrahydrofuran; hydrocarbons, such as cyclohexane, toluene, benzene; halohydrocarbons, such as methylene chloride, chloroform, chlorobenzene; phenol; acetone; dimethylsufone or N,N-dimethylformamide, and the like; and the mixtures thereof.

The present method is suitable for either continuous or batch crystallization processes, The circulating amount of the slurry is determined by the crystallization system and the desired crystal size distribution of the crystalline product. In general, the circulating amount of the slurry in a continuous crystallization process is 3 to 10 times of the handling capacity of the crystallizer, while in a batch crystallization process the circulating amount per hour is 0.5 to 15 times of the loading amount of the crystallizer. The time of the circulation is equal to the time of crystallization.

The present invention is illustrated in more details with reference to the accompanying drawings.

DETAILED DESCRIPTION OF THE INVENTION

Figure 1:
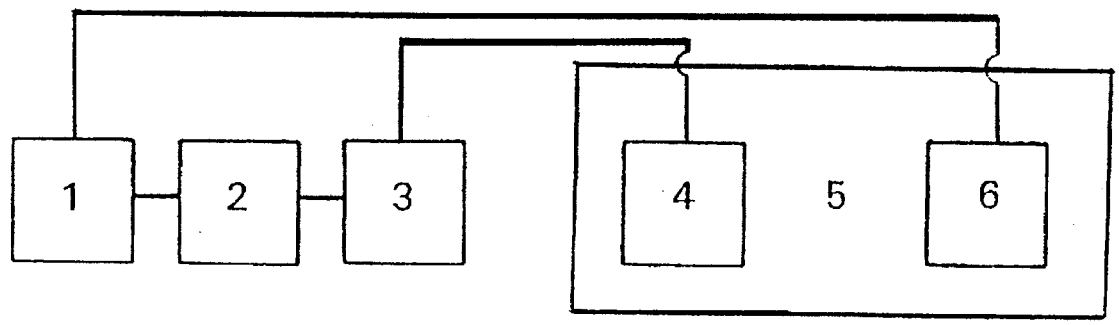
FIG. 1 is a schematic diagram of an embodiment of the present invention, wherein 1 and 3 are fines destructors, 2 is circulating pump, 4 and 6 are filters and 5 is crystallizer.

In FIG. 1, a slurry containing only fines of a size smaller than the fines cut size is drawn from cystallizer 5, through filter 4 in crystallizer 5, to fines destructor 3, wherein the fines are dissolved by heating or increasing solvent the dissolved mixture then passes through circulating pump 2 and fines destructor 1 to filter 6 in crystallizer 5, thereby washing filter 6, and finally back to crystallizer 5. After an interval, the above mentioned process rims in opposite direction, i.e. a slurry containing only the fines of a size smaller than the fines cut size is drawn from crystallizer 5, through filter 6 in crystallizer 5, to fines destructor 1 wherein the fines are dissolved by heating or increasing solvent. The dissolved mixture then passes through circulating pump 2 and fines destructor 3 to filter 4 in crystallizer 5, thereby washing filter 4, and finally back to crystallizer 5. The above mentioned process is switched over at regular intervals and runs continuously with a length of switching interval depending on the materials to be crystallized and the type of the crystallization process.

Figure 2:
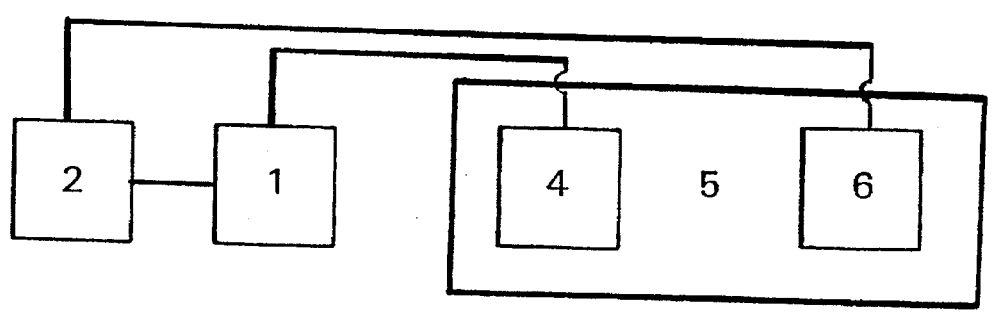
FIG. 2 is a schematic diagram of another embodiment of the present invention, wherein 2 is circulating pump, 1 is fines destructor, 4 and 6 are filters and 5 is crystallizer.

In FIG. 2, a slurry containing only fines of a size smaller than the fines cut size is drawn from crystallizer 5, through filter 4 in crystallizer 5, to fines destructor 1 wherein the fines are dissolved by heating or increasing solvent. The dissolved mixture then passes through circulating pump 2 to filter 6 in crystallizer 5, thereby washing filter 6, and finally back to crystallizer 5. After an interval, the above-mentioned process runs in opposite direction, i.e. the slurry containing only fines of a size smaller than the the fines cut size is drawn from crystallizer 5, through filter 6 in crystallizer 5 and circulating pump 2 to fines destructor 1 wherein the fines are dissolved by heating or increasing solvent. The dissolved mixture then passes through filter 4 in crystallizer 5, thereby washing filter 4, and finally back to crystallizer 5. The above-mentioned process is switched over at regular intervals and runs continuously.

Another aspect of the present invention is the preparation of bisphenol A product with high purity by applying the above method of the present invention to the production process of bisphenol A. Thus, the present invention furthermore provides new method for preparing crystalline bisphenol A/phenol adduct or crystalline bisphenol A with high purity and large crystal size. The said method comprises the following steps:

A. two filters are installed in a crystallizer;

B. a part of the slurry containing crystalline bisphenol A/phenol adduct or crystalline bisphenol A is filtered through the first filter using a circulating pump, and a slurry containing fines, substantially all of which are of a size smaller than the fines cut size, is fed into at least one fines destructor in which they are dissolved, and then the solution in which the fines have been destructed is fed back to the crystallizer through the second filter for further crystallization;

C. after a switching interval, a part of the slurry containing crystalline bisphenol A/phenol adduct or bisphenol A is filtered through the second filter using the circulating pump and a slurry containing fines, substantially all of which are of a size smaller than the fines cut size is fed into at least one fines destructor in which they are dissolved, and then the solution in which the fines have been destructed is fed back to the crystallizer through the first filter for further crystallization, thereby washing the first filter; and D. after a switching interval, repeating the procedure B, thereby washing the second filter, and continuing to alternately repeat the procedures B and C to carry out the process of destructing fines continuously.

The crystallizers, filters and fines destructors used in the present method are the same as described above.

In the present method, either one or two fines destructors may be used. When two destructors are used, they may or may not be the same, and the circulating pump is located between them; when one destructor is used, the circulating pump may be located either before or behind it.

The present method is suitable for either continuous or batch crystallization processes. The circulating amount of the slurry is dependent on the materials to be crystallized and the desired crystal size distribution of the crystalline product. In general, the circulating amount of the slurry is 3–10 times of the handling amount of the crystallizer in the continuous crystallization process, while the circulating amount of the slurry per hour is 0.5 to 15 times of the loading amount of the crystallizer in the batch crystallization process. The time of circulation is equal to the time of crystallization.

Comparing with the prior art, the present invention has the following advantages:

1. Through a filter installed in a crystallizer, a slurry containing only fines of size smaller than the fines cut size is drawn from the crystallizer, through a fines destructor wherein the fines are dissolved, back to the crystallizer. The above process is simple and effective not requiring any change of the original crystallizer. The fines cut sizes can be controlled by selecting the covering knitmesh materials with different pore size.
2. There are two filters in the crystallizer. The slurry is drawn from one filter to the fines destructor for dissolving fines, then through another filter to wash it and finally fed back to the crystallizer. The two filters are switched over and washed at regular intervals to prevent blockage and ensure the continuous operation of the process
3. There may be a fines destructor at each said before and behind the circulating pump. This arrangement keeps crystals from entering the circulating pump and hence the requirement to the quality of the pump is less hard.
4. The crystal size and its distribution in the crystallizer can be effectively controlled by regulating the flow rate of the circulating fines slurry, and a crystalline product with uniform and large crystal size and high purity is obtained.
5. The present method for destructing fines is applicable to many types of crystallizer to carry various crystallization process. It is particularly suitable to the crystallization system in which the density difference between sold and liquid is small. The method is convenient and reliable, having no need of complicated apparatus. The crystalline product is of high purity and uniform and large crystal size.

BEST MODE FOR CARRYING OUT THE INVENTION

The invention is further illustrated by the following Examples which should not be regarded as limiting to the spirit and scope of the present invention.

EXAMPLE 1

A solution of bisphenol A/phenol(64.36% by weight of phenol, 34.29% by weight of bisphenol A, 0.64% by weight of 2.4-bisphenol A, 0.30% by weight of water, 0.30% by weight of triphnol, 0.07% by weight of chroman and 0.04% by weight of others) at 85° C. was fed to a continuous MSMPR cooling crystallizer at a rate of 20 kg/hr to obtain a slurry containing crystalline bisphenol A/phenol adduct. The residence time in crystallizer is 270 min., operation temperature is 42° C. After filtering and washing the slurry, a crystalline bisphenol A/phenol adduct with a mean crystal size of 210 µm, variation coefficient of 37% and purity of 99.9% was obtained.

Using the embodiment of the present invention shown in FIG. 1 two porous hollow cylinder filters made of stainless steel were installed vertically at the ⅔ of the height of the MSMPR crystallizer. The filters have a length of 250 mm and a diameter of 80 mm. There are plenty of holes with a diameter of 5 mm and a separation of 10 mm on the filters which are covered by stainless steel screen of 120 mesh. A shell and tube fines destructor was installed at each side before and behind a circulating pump (type w-3), and hot water of 85° C. passed the tube side of the destructor. A slurry containing only fined of size smaller then 125 um was fed to the shell side of the destructor from the crystallizer through the first filter at a rate of 120 kg/hr for dissolving fines by heating, and returned to the crystallizer through the second filter after dissolving fines. The interval of switching from one filter to the other was 35 min., and the crystallization process in the crystallizer was the same as described above. After filtering and washing the slurry, a crystalline bisphenol A/phenol adduct with a mean crystal size of 390 µm, variation coefficient of 21% and purity of 99.99% was obtained. Comparing with the product obtained without using the operation of destructing fines, the crystal size of the product increased by 85.7% and the variation coefficient by 43%, moreover the purity was improved significantly

EXAMPLE 2

A solution of bisphenol A (29.42% by weight of bisphenol A, 68.62% by weight of toluene and 1.96% by weight of water) was crystallized in a batch DP (Double propeller) cooling crystallizer. The loading amount per batch was 30 kg, residence time was 200 min., and the initial and final temperatures in crystallization were 85° C. and 35° C. respectively.

Using the embodiment of the present invention shown in FIG. 1, two rectangular (150×40×mm) hollow filters made of stainless steel were installed vertically at the ½ of the height of the crystallizer. There were plenty of 6 mm diameter holes arranged in a pattern of square with a separation of 10 mm on the wall of the fiters which were covered with a stainless steel screen of 80 mesh.

A jacketed fines destructor with stirrer was installed at each side before and behind a circulating pump (stainless steel vortex pump), and hot water of 90° C. passed the jacket of the destructor. A slurry containing only fines of size smaller than 180 µm was drawn from the crystallizer at a variable rate of 25 to 50 kg/hr., through one of the filters to the destructor for dissolving fines, and then returned the crystallizer through another filter. The interval of switching from one filter to the other was 15 mims.

The slurry from the crystallizer was centrifugated and washed after finishing the process of a batch, a crystalline bisphenol A with a mean crystal size of 1200 µm, variation coefficient of 28% and purity of 99.99% by weight was obtained.

The same crystallization operation was carried out by using the above equipment, except that no fines destruction system was used. A crystalline bisphenol A with a mean crystal size of 850 µm, variation coefficient of 43% and purity of 99.90% was obtained.

EXAMPLE 3

An aqueous KCL solution was fed to a batch evaporating crystallizer with a stirrer for evaporating crystallization. The loading amount per batch was 50 kg and the residence time was 135 mins.

Using the embodiment shown in FIG. 2, two hollow ellipsoid filters having a length of 200 mm, major diameter of 60 mm and a minor diameter of 30 mm, were installed at the ½ of the crystallizer height. There were plenty of circular holes with a diameter of 6 mm and a separation of 8 mm on the filters which were covered with Nylon filter cloth of 60 mesh. A slurry containing only the fines of size smaller than 250 μm was drawn from the crystallizer in a variable rate of 70 to 180 kg/hr., through one of the filters, into an electro-heating kettle installed before a single-screw pump to carry out the process of destructing fines, and then fed back to the crystallizer. The interval of switching from on filter to another is 25 mins.

After filtering and washing the slurry, a crystalline product with a mean crystal size of 904 μm, purity of 99.97% and variation coefficient of 23% was obtained. In contrast, a crystalline product with a mean crystal size of 725 μm, purity of 99.85%, variation coefficient of 41% was obtained When no operation of destructing fines was used. The crystalline product obtained by using the present method shown an increase of 24.7% in crystal size and a decrease of 43.9% in variation coefficient.

EXAMPLE 4

An aqueous solution of $Na_2SO_4$ was fed to a batch operating vacuum crystallizer for crystallization. The loading amount per batch was 40 kg and the residence time was 330 mins. The initial and final temperatures in crystallzation process were 42° C. and 7° C., respectively.

Using the embodiment shown in FIG. 2, two ellipsoid hollow cylinder filters with a length of 200 mm, major diameter of 80 mm and minor diameter of 40 mm were installed in the crystallizer. There were plenty of holes with a diameter of 6 mm and a separation of 10 mm on the filters, which are covered with Nylon filter cloth of 80 mesh, installed vertically at the upper part of the crystallizer and immersed in solution.

Circulation water of 45° C. passed a coil heat exchanger installed before a circulating pump. A slurry containing only fines of size smaller than 180 μm was drawn from the crystallizer in a variable rate of 20 to 80 kg/hr to the heat exchanger for destructing fines, and then fed back to the crystallizer. The interval of switching from one filter to another is 45 mins.

After finishing the operation of a batch, the slurry was filtered under suction and washed, and a crystalline product with a mean crystal size of 800 μm, variation coefficient of 20% and purity of 99.98% was obtained. Repeating the above operation, except that no operation of destructing fines was used, a crystalline product with a mean crystal size of 620 μm, variation coefficient of 89% and purity of 99.85% was obtained.

We claim:

1. A method for obtaining large crystals by destructing fines in a slurry in a crystallizer, the method comprising:
   A. installing first and second filters in the crystallizer;
   B. filtering a part of the slurry in the crystallizer through the first filter using a circulating pump, and feeding a slurry containing fines, all of which are of a size smaller than the fines cut size to at least one fines destructor in which they are dissolved, and then returning the solution in which the fines have been destructed to the crystallizer through the second filter for further crystallization;
   C. after a switching interval, filtering a part of the slurry in the crystallizer through the second filter using the circulating pump, and feeding a slurry containing fines, substantially all of which are of a size smaller than the fines cut size to at least one fines destructor in which they are dissolved, and then returning the solution in which the fines have been destructed to the crystallizer through the first filter for further crystallization, thereby washing the first filter; and
   D. after a switching interval, repeating the procedure B and thereby washing the second filter, and continuing to alternately repeat the procedures B and C to carry out the process of destructing fines continuously.

2. A method according to claim 1, wherein the first and second filters are installed in the crystallizer and connected with a single fines destructor.

3. A method according to claim 1, wherein the direction of circulation through the first and second filters is switched over at regular intervals to alternately wash the filters and to ensure the continuous operation of the crystallization process.

4. A method according to claim 1, wherein said filters comprise a porous hollow cavity with or without a metal screen cover, a glass fiber screen or knitmesh made of synthetic or natural fibers.

5. A method according to claim 1, wherein said fines destructor is a shell and tube exchanger, coil heat exchanger or jacketed heat exchanger.

6. A method according to claim 1, wherein the said crystallizer is a vacuum crystallizer, cooling crystallizer, evaporating crystallizer, salting crystallizer or reaction crystallizer.

7. A method according to claim 1, wherein the crystallization process using said method is a continuous or a batch process.

8. A method according to claim 1, wherein said slurry is a solute-solvent system.

9. A method for preparing crystalline bisphenol A/phenol adduct or bisphenol A with high purity and large crystal size, comprising the steps of:
   A. installing first and second filters in the crystallizer;
   B. filtering a part of the slurry containing crystalline bisphenol A/phenol adduct or bisphenol A through the first filter using a circulating pump, feeding a slurry containing fines, substantially all of which are of a size smaller than the fines cut size, to at least one fines destructor in which the are dissolved, and returning the solution in which the fines have been destructed to the crystallizer through the second filter for further crystallization;
   C. after a switching interval, filtering a part of the slurry containing crystalline bisphenol A/phenol adduct or bisphenol A through the second filter using a circulating pump and feeding a slurry containing fines, substantially all of which are of a size smaller than the fines cut size to at least one fines destructor in which said fines are dissolved and returning the solution in which the fines have been destructed to the crystallizer through the first filter for further crystallization thereby washing the first filter; and
   D. after a switching interval, repeating the step B, thereby washing the second filter, and continuing to alternately repeat the procedures B and C to carry out the process of destructing fines continuously.

10. A method according to claim 9, wherein the first and second filters are installed in the crystallizer and connected with a single fines destructor.

11. A method according to claim 9, wherein the direction of circulation through the first and second filters is switched over at regular intervals to alternately wash each filter and to ensure the continuous operation of the crystallization process.

12. A method of claim 9, wherein the said filters are of porous hollow cavity and are covered with a metal screen, a glass fiber screen or knitmesh made of synthetic or natural fibers.

13. A method according to claim 9, wherein said fines destructor is a shell and tube exchanger, coil heat exchanger or jacketed heat exchanger.

14. A method according to claim 9, characterized in that the said crystallizer is a vacuum crystallizer, cooling crystallization or evaporating crystallizer.

15. A method according to claim 9, wherein said crystallization takes place in a continuous or a batch process.

* * * * *

UNITED STATES PATENT AND TRADEMARK OFFICE
CERTIFICATE OF CORRECTION

PATENT NO. : 5,663,456
DATED : September 2, 1997
INVENTOR(S) : Zhang et al

It is certified that error appears in the above-identified patent and that said Letters Patent is hereby corrected as shown below:

In claim 12, column, 9, line 1, delete "of" (first occurrence) and insert --according to--.

In claim 14, column 10, line 1, delete "characterized in that the" and insert --wherein--.

Signed and Sealed this

Thirtieth Day of December, 1997

Attest:

BRUCE LEHMAN

*Attesting Officer*     *Commissioner of Patents and Trademarks*